United States Patent [19]

Berman et al.

[11] Patent Number: 4,668,803
[45] Date of Patent: May 26, 1987

[54] BENZAFURAN DERIVATIVES

[75] Inventors: Elliot Berman, Los Angeles, Calif.; Brian A. Zentner, Newton Center, Mass.

[73] Assignee: Atlantic Richfield Company, Los Angeles, Calif.

[21] Appl. No.: 750,656

[22] Filed: Jul. 1, 1985

Related U.S. Application Data

[63] Continuation of Ser. No. 608,841, May 10, 1984.

[51] Int. Cl.$^4$ ............ C07D 309/30; C07D 407/04; C07D 315/00; C07D 221/18
[52] U.S. Cl. .................. 549/291; 549/414; 549/467; 546/166; 546/196; 546/72; 136/247; 350/96.10; 250/483.1; 250/227; 372/53; 252/301.17; 252/301.16; 548/950; 540/480; 540/596
[58] Field of Search .......... 549/467, 291, 419, 414; 136/247; 350/96.10; 250/483.1, 227; 372/53; 252/301.17, 301.16

[56] References Cited

U.S. PATENT DOCUMENTS

| | | | |
|---|---|---|---|
| 3,798,566 | 3/1974 | MacColgin et al. | 331/94.5 L |
| 3,852,683 | 12/1974 | Webster et al. | 331/94.5 L |
| 3,880,886 | 4/1975 | Koch | 549/283 |
| 4,492,778 | 1/1985 | Claussen et al. | 136/247 |

FOREIGN PATENT DOCUMENTS 50-40627  5/1975  Japan .............. 252/301.16

OTHER PUBLICATIONS

Davidson, et al., Chem. Abstracts, vol. 88; 5700e (1978).
Mehlhorn et al, Chem. Abstracts, vol. 89; 146215h (1978), ibid, vol. 87; 200566x (1977).

Primary Examiner—Henry R. Jiles
Assistant Examiner—J. Richter
Attorney, Agent, or Firm—Roderick W. MacDonald

[57] ABSTRACT

Novel organic compound of the basic formula

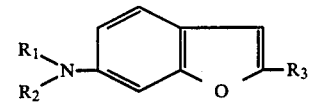

which have substantial luminescent emission characteristics and advantages.

2 Claims, No Drawings

BENZAFURAN DERIVATIVES

This application is a continuation, of application Ser. No. 608,841, filed May 10, 1984.

BACKGROUND OF THE INVENTION

Heretofore, numerous organic compounds which have fluorescent capabilities, i.e., the ability to absorb light of one energy wavelength and then remit light of a different lower energy wavelength, have found a number of practical uses such as in dye lasers, luminescent solar concentrators, fluorescent paints, inks, and other obvious applications.

BRIEF SUMMARY OF THE INVENTION

In accordance with this invention, novel organic compounds have been developed which not only have luminescent emission capabilities, but also exhibit certain very beneficial characteristics which are quite advantageous in the prior art applications of such materials. For example, the compounds of this invention absorb visible light and have substantial stability to that visible light while efficiently luminescing with a substantial Stokes shift, i.e., wavelength shift between around state absorption and luminescent emission. For example, shifts of 100 nanometers or more can be obtained by the compounds of this invention so that the light reemitted by these compounds is not readily reabsorbed by the compounds themselves. Further, in addition to a large Stokes shift capability, these compounds have a high quantum efficiency for luminescence and good stability to visible light. This is brought about, at least in part, by locking in the geometry of a key double bond as will be described in greater detail hereinafter.

Accordingly, it is an object of this invention to provide novel organic compounds with substantial luminescent advantages.

It is another object to provide new and improved dye lasers, luminescent solar collectors, and the like employing such organic compounds.

Other aspects, objects and advantages of this invention will be apparent to those skilled in the art from this disclosure and the appended claims.

DETAILED DESCRIPTION OF THE INVENTION

It has been discovered that the prior art compositions such as

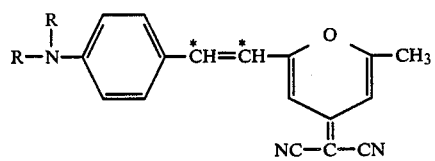

although exhibiting good Stokes shifts also experienced decreased quantum efficiency of luminescence because, it is thought, of the competing photochemical cis-trans isomerization at the carbons marked "*". Further, such materials tend to degrade photochemically following a route that also involves the cis-trans isomerization phenomenon.

The compounds of this invention avoid such cis-trans isomerization problems by making the carbons marked "*" above part of a furan ring system.

Accordingly, the organic compounds of this invention are of the general structure:

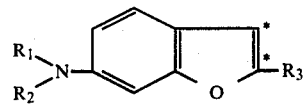

wherein $R_1$ and $R_2$ can be unbonded to one another or bonded to one another; when unbonded to one another $R_1$ and $R_2$ can be the same or different and are selected from the group consisting of hydrogen, and alkyl radicals having from 1 to 10 carbon atoms per molecule; when bonded to one another $R_1$ and $R_2$ are selected from the group consisting of cycloalkyl radicals

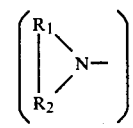

having from 2 to 20 carbon atoms per molecule, and

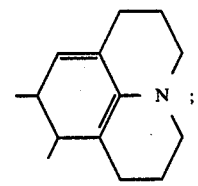

and $R_3$ is selected from the group consisting of

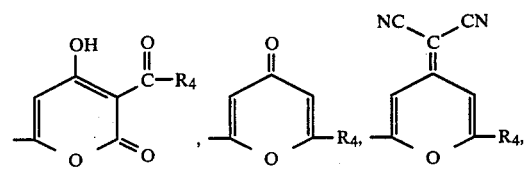

where $R_4$ is an alkyl radical having from 1 to 10 carbon atoms per molecule, and

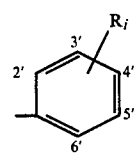

where $R_i$ is one or more substituents selected from the following table so that the expression $$\sum_{2' \leq q \leq 6'} \sigma(R_i, q),$$

where q represents the substituent positions 2′, 3′, 4′, 5′, and 6′, is positive.

Substituent Constant Sigma Values = σ

| $R_i$ | Ring Positions | | |
|---|---|---|---|
| | 2′, 6′ | 3′, 5′ | 4′ |
| $CH_3$ | −0.17 | −0.069 | −0.306 |
| $CH_2CH_3$ | −0.16 | −0.0625 | −0.291 |
| $CH(CH_3)_2$ | −0.15 | −0.0589 | −0.276 |
| $C(CH_3)_3$ | −0.14 | −0.0581 | −0.250 |
| $C_6H_5$ | 0.00 | +0.06 | −0.01 |
| $CF_3$ | — | +0.43 | +0.54 |
| $CN$ | — | +0.56 | +0.66 |
| $COCH_3$ | — | +0.376 | +0.502 |
| $CO_2C_3H_5$ | — | +0.37 | +0.45 |
| $CO_2H$ | — | +0.37 | +0.45 |
| $NH_2$ | — | −0.16 | −0.66 |
| $NHCH_3$ | — | — | −0.84 |
| $N(CH_3)_2$ | — | — | −0.83 |
| $NHCOCH_3$ | — | +0.21 | 0.0 |
| $NO_2$ | +0.80 | +0.662 | +0.777 |
| $OCH_3$ | −0.39 | +0.0465 | −0.764 |
| $OC_2H_3$ | −0.35 | +0.1 | −0.24 |
| $O(CH_2)_2CH_3$ | — | +0.1 | −0.25 |
| $O(C_6H_5)$ | — | +0.252 | −0.32 |
| $OH$ | — | +0.121 | −0.37 |
| $OCOCH_2$ | — | +0.39 | +0.31 |
| $SCH_3$ | — | +0.15 | 0.0 |
| $SH$ | — | +0.25 | +0.15 |
| $SCOCH_3$ | — | +0.39 | +0.44 |
| $SCN$ | — | — | +0.52 |
| $SOCH_3$ | — | +0.52 | +0.49 |
| $SO_2CH_3$ | — | +0.60 | +0.72 |
| $SO_2NH_2$ | — | +0.46 | +0.57 |
| $F$ | +0.24 | +0.337 | −0.0714 |
| $Cl$ | +0.20 | +0.373 | +0.112 |
| $BR$ | +0.21 | +0.391 | +0.148 |
| $I$ | +0.21 | +0.352 | +0.132 |
| $IO_2$ | — | +0.70 | +0.76 |
| $CH_2CH=CH_2$ | −0.16 | −0.0625 | −0.291 |
| $CO_2CH_3$ | +0.45 | +0.37 | +0.45 |

An exemplary, but not all inclusive, listing of compounds in this invention is 2-6(3-acetyl-4-hydroxy-2-pyrone)-6-(N,N diethylamino)-benzofuran; 2-6(3-butyryl-4-hydroxy-2-pyrone)-6-(N-piperidino)-benzofuran; 10-6(3-propionyl-4-hydroxy-2-pyrone)-1H,5H-benzofurano-2,3,6,7-tetrahydroquinolizine; 2-2(6-methyl-4-pyrone)-6-(N,N-dimethylamino)-benzofuran; 2-2(6-methyl-4-pyrone)-6-(N-piperidino)-benzofuran; 10-2(6-methyl-4-pyrone)-1H,5H-benzofurano-2,3,6,7-tetrahydroquinolizine; 2-2(6-methyl-4-dicyanomethylene-4-pyran)-6-(N,N-diethylamino)benzofuran; 2-2(6-methyl-4-dicyanomethylene-4-pyran-6-(N-piperidino)-benzofuran; 2-2(6-methyl-4-dicyanomethylene-4-pyran)benzofurano-6,7,8,9-tetrahydro quinoline; 10-2(6-methyl-4-dicyanomethylene-4-pyran)-1H,5H-benzofurano-2,3,6,7-tetrahydroquinolizine; 2-2(6-methyl-4-dicyanomethylene-4-pyran)-6-(N-pyrrolidino)-benzofuran; 2-(4-nitrophenyl)-6-(N,N-dimethylaminobenzofuran; 2-(4-nitrophenyl)-6-N-piperidino-benzofuran; 10-(4-nitrophenyl)-6-1H,5H-benzofurano-2,3,6,7-tetrahydro-quinolizine; 10-(2,4-dinitrophenyl)-6-1H,5H-benzofurano-2,3,6,7-tetrahydro-quinolizine; 10-(2-4-dinitrophenyl)-6-benzofurano-2,3,6,7-tetrahydro-quinolizine; 10-(3-nitrophenyl)-6-benzofurano-2,3,6,7-tetrahydro-quinolizine; 10-(3-chloro-4-nitrophenyl)-6-benzofurano-2,3,6,7-tetrahydro-quinolizine; 10-(4-trifluoromethylphenyl)-6-benzofurano-2,3,6,7-tetrahydro-quinolizine; 10-(3,5 dichlorophenyl)-6-benzofurano-2,3,6,7-tetrahydro-quinolizine; 2-(3,5-dihydroxyphenyl)-6-N-piperidinobenzofuran; 2-2(6-methyl-4-cyanoacetate methylene-4 pyran)-6-(N,N-dimethylamino)benzofuran; 2-(4′-dicyanomethylene-2′-methyl-α-pyran)-6-dimethylaminobenzofuran; 2-(4′-hydroxy-3′-acetyl-α-pyrone)-6-dimethylaminobenzofuran; +2-(p-nitrophenyl)-6-dimethyaminobenzofuran.

One skilled in the art being apprised of the foregoing structures and specific compounds will readily be able to determine one or more methods for producing such compounds. However, even though this is so, it would be of help to those skilled in the art in the preparation of such compounds if specific examples are set forth of the preparation of several such compounds within this invention.

The first example involves the preparation of 2-(4′-Dicyanomethylene-2′-Methyl-gamma-pyran)-6-Dimethylaminobenzofuran.

4-Dicyanomethylene-2-6-Dimethyl-γ-pyran (4.3 g, 0.025 mole) was added to N-bromosuccinimide (4.65 g, 27.5 m mole), carbon tetrachloride (100 ml), and benzoyl peroxide (0.2 g). The mixture was refluxed under a 300 watt lamp for 4 hours. The reaction was cooled, 100 ml of carbon tetrachloride was added, and the mixture was stored in the cold overnight. It was then filtered and the solvent evaporated, leaving a residue, 5.5 g (88%). No purification was carried out. Instead, the produced was used immediately in the next step.

The brominated product (5.5 g, 0.022 mole), dimethyl amino salicylaldehyde (3.6 g, 0.022 mole), potassium carbonate (3.35 g, 0.024 mole), and methanol (40 ml) were refluxed for 7 hours. The methanol was evaporated, the residue extracted with ether in a Soxhlet, ether evaporated, residue purified by chromatography (silica gel/chloroform) and recrystallized from acetonitrile, giving solid with melting point 293–295.

| Solvent | λ max nm | λ lum$_{max}$ |
|---|---|---|
| dioxane | 453 | 550 |
| benzene | 459 | 540 |
| $Et_2O$ | 450 | 548 |
| $CHCl_3$ | 472 | 563 |
| EtOAc | 457 | 586 |
| THF | 461 | 587 |
| $CH_2Cl_2$ | 468 | 585 |
| acetone | 459 | 615 |
| EtOH | 467 | 625 |
| $CH_3CN$ | 458 | 622 |

The compound 2-(4′Hydroxy-3′-acetyl-alpha-pyrone)-6-Dimethylaminobenzofuran was prepared as follows.

Dehydroacetic acid (4.2 g, 0.025 mole) was added to carbon tetrachloride (100 ml) in a flask equipped with a magnetic stirrer, a thermometer and a liquid nitrogen condenser. Bromine (1.3 ml, d. 3.12, 0.025 mole) was added, then benzoyl peroxide (0.2 g, catalyst) and the contents were stirred and exposed to a 300 watt lamp set 2 cm from the flask and using aluminum foil as a surrounding reflector. The contents refluxed at 80° C. and were stirred for one hour, after which the bromine color had faded to light yellow. The solvent was evaporated and the residue dried under high vacuum. The crude mixture was not purified.

Brominated dehydroacetic acid (2 g, mixture of 4.8 mmole brominated and 4.8 mmole starting material) was added to 4-dimethylaminosalicylaldehyde (0.8 g, 4.8 mmole) in a flask. Potassium carbonate (1.3 g, 9.4 mmole anhydrous) was placed in a crucible over a flame for 10 minutes, then added to the mixture, followed by methanol (50 ml). The flask contents were refluxed with stirring for 16 hours, then poured into 100 ml of water.

The solution (pH 8) was acidified with hydrochloric acid (to pH 6), then extracted with dichloromethane (3×250 ml). The extracts were combined, dried with magnesium sulfate, filtered, and evaporated. The residue was placed in a Soxhlet apparatus and extracted with heptane for 48 hours. The heptane was evaporated and the residue was eluted on a dry silica column with ether. Certain fractions which eluted produced crystals on partial evaporation of the ether.

Red crystals (as small needles). M.P. 214°-215° C.
I.R. (CHCl$_3$): 1725 cm$^{-1}$ (carbonyl), 1610 cm$^{-1}$ (aromatic), 1035 cm$^{-1}$ (aromatic), 1350 cm:$^{-1}$ (Me$_2$—N—$\phi$).

Elemental analysis:
C$_{17}$H$_{15}$NO$_5$ mol wt: 313.31

| calculated: | C 65.17 | H 4.83 | N 4.47 |
| --- | --- | --- | --- |
| found: | 64.88 | 4.85 | 4.32 |
| Solvent | λ max nm | λ lum$_{max}$ | |
| benzene | 457 | 530 | |
| ether | 450 | 535 | |
| dioxane | 450 | 538 | |
| THF | 457 | 570 | |
| chloroform | 463 | 552 | |
| CH$_2$Cl$_2$ | 461 | 572 | |
| EtOAc | 453 | 565 | |
| ethanol | 455 | 605 | |
| acetonitrile | 453 | 603 | |
| acetone | 455 | 595 | |

The compound 2-(p-nitrophenyl)-6-Dimethylaminobenzofuran was prepared as follows.

p-Dimethylaminosalicylaldehyde was prepared from p-dimethylaminophenol (Aldrich Chemical Co.) by the procedure of W. C. Baird and R. L. Shriner, Journal American Chemical Society, 86, 3142 (1964). p-Nitrobenzylbromide (VI) (Aldrich Chemical Co., 2.5 g, 0.012 mole) was added to dimethylaminosalicylaldehyde (1.9 g, 0.012 mole), potassium carbonate (3.2 g, 0.024 mole, ignited, and methanol (60 ml). The mixture was refluxed for 20 hours, then cooled and the solvent evaporated. The residue was ground into a powder and extracted in a Soxhlet with ether (300 ml) for 2 days. The ether was evaporated and the solid recovered. M.P. 206-207, R$_f$ 0.50 (CHCl$_3$ on silica). Yield 0.7 g (recryst. from CHCl$_3$)
I.R. (CHCl$_3$) 1110 cm$^{-1}$, 1340 cm$^{-1}$ (—NO$_2$), 1590 cm$^{-1}$ (—NO$_2$), 1625 cm$^{-1}$ The structure of III was confirmed by proton magnetic resonance spectroscopy.

| Solvent | λ max nm | λ lum$_{max}$ |
| --- | --- | --- |
| hexane | 423 | 477/507 |
| benzene | 435 | 590 |
| ether | 433 | 595 |
| dioxane | 432 | 610 |
| CCl$_4$ | 433 | 545 |

The compounds of this invention have utility in any number of obvious applications, particularly fluorescent applications. For example, the compounds can be used as the dye in dye lasers such as those disclosed in U.S. Pat. Nos. 3,852,683 and 3,798,566. The compounds can also be employed in fluorescent printing mediums such as ink, paint, and the like for application to signage, particularly outdoor signs. Also, the compounds can be employed to substantial advantage in luminescent solar concentrators.

A luminescent solar concentrator (LSC) is a planar layer of materials, contained in a transparent matrix, which reemit light after absorption of light. A portion of the reemitted light is trapped within the matrix and can escape only at the layer edges (FIG. 1). The fraction trapped can be calculated from Snell's law to be $$\frac{4(n^2 - 1)^{\frac{1}{2}}}{(n + 1)^2}$$

where n is the refractive index of the matrix (FIG. 2). The maximum concentration possible is the ratio of the planar area to that of the edges.

The advnatages of an LSC are that it collects and concentrates diffuse as well as direct radiation; eliminates heat dissipation problems of solar optical concentrators since excess energy of short wavelength radiation and non-useful long wavelength radiation is not focused on the converter; separates light absorption and light conversion functions; and allows more efficient use of narrow spectral response converters.

The amount of one or more of the compounds of this invention employed in any of the foregoing or other obvious applications will vary considerably and therefore cannot be specified here, but will all be obvious to those skilled in the art once the specific compound or compounds are chosen and the particular utility to which they are to be applied defined.

Reasonable variations and modifications are possible within the scope of this disclosure without departing from the spirit and scope of this invention.

What is claimed is:

1. Organic compounds of the structure wherein:

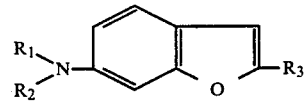

wherein
R$_1$ and R$_2$ are unbonded to one another, and can be the same or different and are selected from the group consisting of hydrogen, and alkyl radicals having from 1 to 10 carbon atoms per molecule, and
R$_3$ is selected from the group consisting of

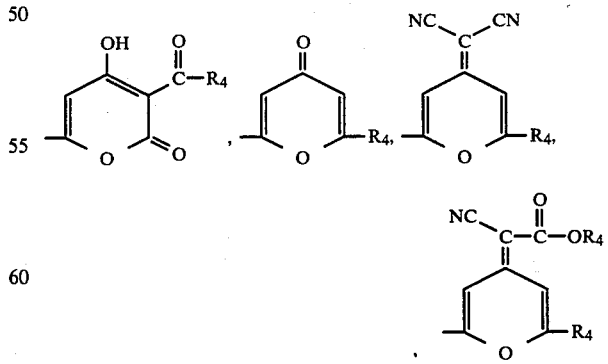

wherein
R$_4$ is selected from the group consisting of alkyl radicals having from 1 to 10 carbon atoms per molecule, and

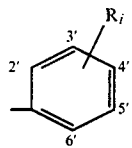

where $R_i$ is one or more substituents selected from the following table so that the expression $$2' \leq \sum_{q} \leq 6' \; \sigma(R_i, q),$$

where q represents the substituent positions 2', 3', 4', 5', and 6', is positive, Substituents Constant Sigma Values = $\sigma$

| $R_i$ | Ring Positions | | |
|---|---|---|---|
| | 2', 6' | 3', 5' | 4' |
| CH₃ | −0.17 | −0.069 | −0.306 |
| CH₂CH₃ | −0.16 | −0.0625 | −0.291 |
| CH(CH₃)₂ | −0.15 | −0.0589 | −0.276 |
| C(CH₃)₃ | −0.14 | −0.0581 | −0.250 |
| C₆H₅ | 0.00 | +0.06 | −0.01 |
| CF₃ | — | +0.43 | +0.54 |
| CN | — | +0.56 | +0.66 |
| COCH₃ | — | +0.376 | +0.502 |
| CO₂C₃H₅ | — | +0.37 | +0.45 |
| CO₂H | — | +0.37 | +0.45 |
| NH₂ | — | −0.16 | −0.66 |

-continued

| $R_i$ | Ring Positions | | |
|---|---|---|---|
| | 2', 6' | 3', 5' | 4' |
| NHCH₃ | — | — | −0.84 |
| N(CH₃)₂ | — | — | −0.83 |
| NHCOCH₃ | — | +0.21 | 0.0 |
| NO₂ | +0.80 | +0.662 | +0.777 |
| OCH₃ | −0.39 | +0.0465 | −0.764 |
| OC₂H₃ | −0.35 | +0.1 | −0.24 |
| O(CH₂)₂CH₃ | — | +0.1 | −0.25 |
| O(C₆H₅) | — | +0.252 | −0.32 |
| OH | — | +0.121 | −0.37 |
| OCOCH₂ | — | +0.39 | +0.31 |
| SCH₃ | — | +0.15 | 0.0 |
| SH | — | +0.25 | +0.15 |
| SCOCH₃ | — | +0.39 | +0.44 |
| SCN | — | — | +0.52 |
| SOCH₃ | — | +0.52 | +0.49 |
| SO₂CH₃ | — | +0.60 | +0.72 |
| SO₂NH₂ | — | +0.46 | +0.57 |
| F | +0.24 | +0.337 | −0.0714 |
| Cl | +0.20 | +0.373 | +0.112 |
| BR | +0.21 | +0.391 | +0.148 |
| I | +0.21 | +0.352 | +0.132 |
| IO₂ | — | +0.70 | +0.76 |
| CH₂CH=CH₂ | −0.16 | −0.0625 | −0.291 |
| CO₂CH₃ | +0.45 | +0.37 | +0.45 |

2. The compounds of claim 1 selected from the group consisting of 2-6(3-acetyl-4-hydroxy-2-pyrone)-6-(N,N-diethylamino)-benzofuran; 2-2(6-methyl-4-pyrone)-6-(N,N dimethylamino)-benzofuran; 2-2(6-methyl-4-dicyanomethylene-4-pyran)-6-(N,N-diethylamino)-benzofuran; 2-2(6-methyl-4-cyanoacetate methylene-4-pyran)-6-(N,N-dimethylamino)benzofuran; 2-(4'-dicyanomethylene-2'-methyl-δpyran-6-dimethylaminobenzofuran; 2-(4'-hydroxy-3'-acetyl-αpyrone)-6-dimethylaminobenzofuran; 2-(p-nitrophenyl)-6-dimethylaminobenzofuran.

* * * * *